United States Patent [19]

Matier et al.

[11] Patent Number: 5,536,749
[45] Date of Patent: Jul. 16, 1996

[54] METHOD FOR ATTENUATION OF SYMPATHETIC NERVOUS SYSTEM ACTIVITY OR ONSET OF MIGRAINE BY SELECTIVELY METABOLIZED BETA-BLOCKING AGENTS

[75] Inventors: William L. Matier, Hockessin, Del.; Ghanshyam Patil, Lincoln University, Pa.

[73] Assignee: SL Pharmaceuticals, Inc., Hockessin, Del.

[21] Appl. No.: 332,590

[22] Filed: Oct. 13, 1994

[51] Int. Cl.[6] .................... A61K 31/235; A61K 31/24; A61K 31/535; A61K 31/505
[52] U.S. Cl. .................. 514/533; 514/534; 514/473; 514/445; 514/415; 514/398; 514/315; 514/256; 514/376; 514/237.5
[58] Field of Search .................... 560/42, 37, 66, 560/110; 514/533, 538, 534, 522, 487, 435, 461, 326

[56] References Cited

U.S. PATENT DOCUMENTS

| | | | |
|---|---|---|---|
| 4,104,402 | 8/1978 | Sugihara et al. | 424/530 |
| 4,190,654 | 2/1980 | Gherardi et al. | 424/244 |
| 4,304,915 | 12/1981 | Berthold | 546/201 |
| 4,346,106 | 8/1982 | Sudilovsky | 424/311 |
| 4,387,103 | 6/1983 | Erhardt et al. | 424/309 |
| 4,402,974 | 9/1983 | Matier et al. | 424/308 |
| 4,428,883 | 1/1984 | Hussain | 424/248.51 |
| 4,453,317 | 6/1984 | Matier | 424/309 |
| 4,454,154 | 6/1984 | Matier | 424/309 |
| 4,501,912 | 2/1985 | Matier et al. | 560/66 |
| 4,503,075 | 3/1985 | Pestellini et al. | 514/622 |
| 4,559,359 | 12/1985 | Matier | 514/522 |
| 4,578,403 | 3/1986 | Matier | 514/522 |
| 4,582,855 | 4/1986 | Kam et al. | 514/487 |
| 4,623,652 | 11/1986 | Erhardt et al. | 514/326 |
| 4,661,513 | 4/1987 | Berthold et al. | 514/459 |
| 4,678,786 | 7/1987 | Roe et al. | 514/247 |
| 4,798,892 | 1/1989 | Kam et al. | 544/146 |
| 4,804,677 | 2/1989 | Erhardt et al. | 514/435 |
| 4,889,856 | 12/1989 | Tolman et al. | 514/254 |
| 4,897,417 | 1/1990 | Patel et al. | 514/461 |
| 4,959,390 | 9/1990 | Patel et al. | 514/522 |
| 4,966,914 | 10/1990 | Patel et al. | 514/461 |

OTHER PUBLICATIONS

Laverdure, B. et al, L'Encephale; XV11: 481–92; (1991).
Besancon, G. et al, L'Ecephale; X1X: 203–7; (1993).
Kallman, Hans O.; Life Sciences, vol. 54, No. 10; pp. 641–644 (1994).

*Primary Examiner*—Richard L. Raymond
*Assistant Examiner*—Deborah Lambkin
*Attorney, Agent, or Firm*—Gildo E. Fato

[57] ABSTRACT

Disclosed is a method for attenuating sympathetic nervous system hyperactivity or onset of migraine in a patient in need of such treatment, by the sublingual, buccal or intranasal administration to such patient of a therapeutically effective amount of a compound of the formula

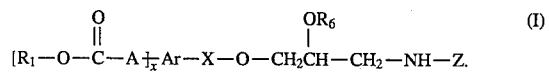

28 Claims, No Drawings

METHOD FOR ATTENUATION OF SYMPATHETIC NERVOUS SYSTEM ACTIVITY OR ONSET OF MIGRAINE BY SELECTIVELY METABOLIZED BETA-BLOCKING AGENTS

BACKGROUND OF THE INVENTION

The present invention relates to a method for attenuating sympathetic nervous system hyperactivity or onset of migraine by the sublingual, buccal or intranasal administration of selectively metabolized beta-blocking agents.

Sympathetic nervous system activation can result in heart rate or blood pressure increases. Activities causing such a result can be physical exertion such as climbing, running or sexual intercourse. Likewise, symptoms such as sweating, tremor and palpitations can result from short-term stressful conditions which might be caused, for example, by "stage fright" because of public speaking, vocal or musical performance or phobias.

Control of heart rate or blood pressure during short-term activities is particularly important for patients at risk due to coronary artery disease such as myocardial ischemic disorders. Severe attacks of chest pain, angina pectoris, occur when cardiac work and myocardial oxygen demand exceed the ability of the coronary arterial system to supply oxygen. The major determinants of myocardial oxygen consumption are heart rate, systolic tension or arterial pressure. Any increase in any of these determinants in the presence of reduced coronary blood flow may induce angina. The higher the blood pressure and the faster the heart rate, the greater the unmet myocardial oxygen need.

Likewise, sympathetic nervous system activation is also an important component of anxiety states in which patients complain primarily of bodily symptoms. These symptoms include palpitations, tremor, difficulty in breathing, sweating, flushing and dizziness. Such anxiety states include: acute stress disorders, as occur from short-term stressful conditions referred to as "stage fright" as in public speaking, vocal or musical performance or examinations; social phobias and panic disorders. Control of bodily symptoms associated with these conditions can alleviate the anxiety state in such patients.

Various drugs have been used to modulate cardiac work in patients with angina pectoris, including vasodilators and beta blockers. Beta blockers are also used in chronic treatment and prophylaxis of anxiety and migraine.

Nitroglycerin is the most commonly used vasodilator to treat angina. It is available in a number of different forms: sublingual tablets that dissolve under the tongue; sublingual sprays; chewable tablets; tablets and capsules for oral administration; ointments and patches for topical administration and solutions for intravenous administration. For treating sudden attacks of angina, the sublingual tablets and sprays and some chewable tablets are most effective. The other nitroglycerin dosage forms, and other nitrate medications, are generally used on a chronic basis to prevent angina attacks from occurring.

Beta blockers such as propranolol are available for chronic treatment and prophylaxis of angina and for other disease states requiring chronic attenuation of sympathetic nervous system hyperactivity, as well as for chronic prophylaxis of migraine. Only one drug, esmolol, is used for acute treatment of sympathetic hyperactivity by intravenous infusion in a hospital setting. These methods possess significant drawbacks for acute prevention or treatment of sympathetic hyperactivity because: prolonged duration of beta blocking action results in greater likelihood of adverse effects in susceptible individuals, such as those with bronchial disease or in diabetes; onset of action may be too slow; chronic beta blocker administration is costly and subjects patients to chronic, undesirable pharmacological actions and the intravenous dosage route is impractical for out of hospital use. Accordingly, there is a need for a method of treatment of acute sympathetic nervous system hyperactivity using beta-blocking agents which are conveniently administered, rapid acting, and have a relatively short duration of action.

Disclosed is a method for administration of selectively metabolized beta-blocking agents to a patient in need of such treatment to attenuate sympathetic nervous system activity or migraine. The method utilizes sublingual, buccal or intranasal administration of such compounds.

SUMMARY OF THE INVENTION

Disclosed is a method for the administration of selectively metabolized beta-blocking agents to a patient in need of such treatment, to attenuate sympathetic nervous system hyperactivity or migraine. The method utilizes sublingual, buccal or intranasal administration of the compounds.

DETAILED DESCRIPTION OF THE INVENTION

The present invention relates to selectively metabolized beta-blocker compounds described by Formula I, which effectively attenuate sympathetic nervous system activity or onset of migraine in mammals when administered by sublingual, buccal and intranasal routes. Because of the relatively rapid metabolism of these compounds, and thereby termination of action by esterases in blood and tissues, rapid onset and rapid offset of systemic beta blocking action can be attained to meet the needs of patients. This can be accomplished by the method described without the undesirable, chronic, pharmacological effects of long-acting agents.

Compounds administered by the method of the present invention are represented by the Formula I:

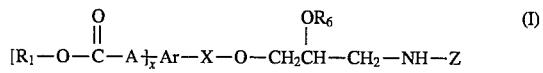

wherein

X is a direct bond —CH$_2$ or

Z is (CH$_2$)$_y$B or

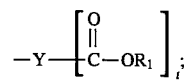

x is 0–3; y is 0–10; t is 0–3;

B, when y is 0, is lower alkyl, lower hydroxyalkyl, lower alkenyl, lower alkynyl or aralkyl;

B, when y is 1–10, is —NR$_2$COR$_3$, —NR$_2$CONR$_3$R$_4$, —NR$_2$SO$_2$R$_3$, —NR$_2$SO$_2$NR$_3$R$_4$ or —NR$_2$COOR$_5$; wherein R$_2$, R$_3$, R$_4$ and R$_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when B is $-NR_2SO_2R_3$ or $-NR_2COOR_5$;

Y is $C_1-C_6$ straight or branched carbon chain, or aralkyl; and

R6 is hydrogen or $-COJ$ wherein J is lower alkyl, wherein R1 is lower alkyl, lower cycloalkyl, lower alkenyl, lower alkynyl, lower alkyl carboxymethyl, aryl carboxymethyl, aryl, or aralkyl;

A is a direct bond, lower alkylene, or lower alkenylene; provided that when x is greater than 1, different occurrences of the

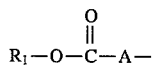

group may be the same or different;

Ar is heterocyclic, unsubstituted aromatic or aromatic substituted with lower alkyl, lower alkenyl, lower alkynyl, lower alkoxy, halogen, acetamido, amino, nitro, lower alkylamino, hydroxy, lower hydroxyalkyl or cyano, lower alkylcarbonyloxy, or pharmaceutically acceptable salts thereof.

Included are compounds of the formula II:

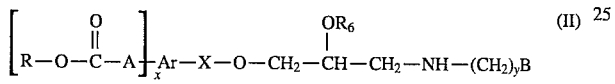 (II)

Included within the compounds of formula II are the compounds of formula IIa as follows:

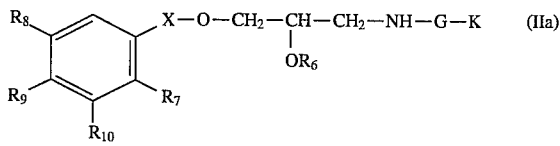 (IIa)

wherein:

$R_7$ is H, $C_1-C_6$ alkyl, $C_2-C_6$ alkenyl, $C_2-C_{10}$ alkynyl, halo, $C_1-C_6$ alkoxy, $C_1-C_6$ cycloalkyl, amino, acylamino, acetamido, nitro, $C_1-C_6$ alkylamino, hydroxy, $C_1-C_6$ hydroxyalkyl, cyano or arylalkoxy wherein the alkyl group includes 1-6 carbon atoms;

$R_8$, $R_9$ and $R_{10}$ are hydrogen or hydroxyl groups or the combination of either hydrogen or hydroxyl groups, or $R_{11}$

wherein $R_{11}$ is $C_1-C_6$ alkyl;

G represents straight or branched alkylene of from 1 to about 10 carbon atoms; and K represents hydrogen, $-NHCOR_{12}$, $-NHCONR_{12}R_{13}$, or $-NHCOOR_{13}$ wherein $R_{12}$ and $R_{13}$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, phenyl which may be unsubstituted or substituted with alkyl of 1 to 6 carbon atoms, furanyl, thiophenyl, imidazole, oxazole or indole, aralkyl wherein the alkyl group contains from 1 to about 6 carbon atoms and the aryl group represents phenyl unsubstituted or substituted with alkyl of from 1 to about 6 carbon atoms, or $R_{13}$ and $R_{14}$ may together with N form a pyrrolidine, piperidine, piperazine, morpholine or thiomorpholine ring and except that $R_{13}$ is not hydrogen when K is $-NHCOOR_{13}$;

$R_{12}$ may be straight or branched lower alkyl, amino, cyclohexyl, morpholino, piperidino, tetrahydrofuranyl, dihydrofuranyl, tetrahydropyranyl, dioxolanyl, 2,2-dimethyl dioxolanyl, dioxanyl, pyrrolidinyl tetrahydroozazolyl, and dihydrooxazolyl, or a pharmaceutically acceptable salt thereof.

Also included within the compounds of formula I are those of formula III:

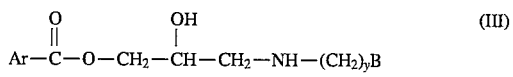 (III)

Preferred compounds are those of formula II wherein X is a direct bond, $R_6$ is H, y is 0, and B is $C_1-C_6$ alkyl, as follows:

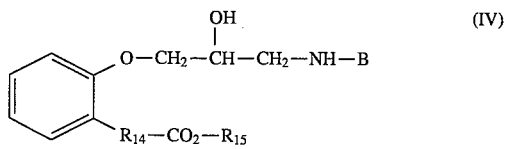 (IV)

wherein $R_{14}$ is a direct bond or $C_1-C_6$ straight or branched alkyl or alkenyl and $R_{15}$ and B are $C_1-C_6$ straight or branched alkyl.

Particularly preferred compounds are those wherein B is isopropyl or t-butyl and $R_{15}$ is methyl or ethyl.

The most preferred compounds are as follows:

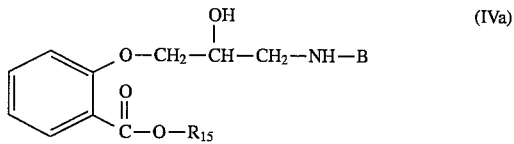 (IVa)

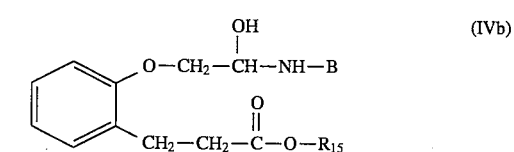 (IVb)

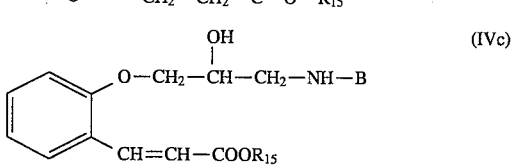 (IVc)

Compounds useful in the present invention may exist as two stereoisomers due to the presence of an asymmetric carbon atom. This invention includes either stereoisomeric form, as well as racemic mixtures. Where Ar is a substituted aromatic ring, substituents claimed may be in the ortho, meta or para positions to the propoxy side chain.

The compounds described in the above formulae may be prepared by any suitable procedure. Compounds prepared as the acid addition salts may be converted to the free base by reaction with an appropriate base such as sodium carbonate or sodium bicarbonate. The compounds of Formula II or III can be advantageously prepared by reacting an appropriate phenol derivative with epichlorohydrin in the presence of a base to form a 1,2-epoxy-3-aryloxypropane derivative as fully described in U.S. Pat. No. 4,804,677, issued Feb. 14, 1989. Reference can also be made to U.S. Pat. Nos. 4,454,154; 4,455,317; 4,559,359; 4,578,403; 4,623,652; or 4,692,446.

Preparation of compounds of Formula III are more fully described, for example, in U.S. Pat. Nos. 4,810,717 issued Mar. 7, 1989. Reference can also be made to U.S. Pat. Nos. 4,402,974; 4,501,912, 4,582,855; or 4,798,892.

For preparation of compounds of Formula II, a reference can be made to U.S. Pat. No. 4,897,417 issued Jan. 30, 1990 or U.S. Pat. Nos. 4,959,390 and 4,966,914.

The procedure described by J. E. Shaffer et al. in *Drug Development Research* 1, 221–232 (1986) was used to assess the potency, onset and duration of beta-blocking action of the compounds of Formula I in anesthetized dogs, except that compositions of Formula I were administered sublingually to the dog instead of by intravenous infusion. Using this method the results shown below were obtained with representative compounds A and B.

The chemical structures of Compounds A and B are as follows:

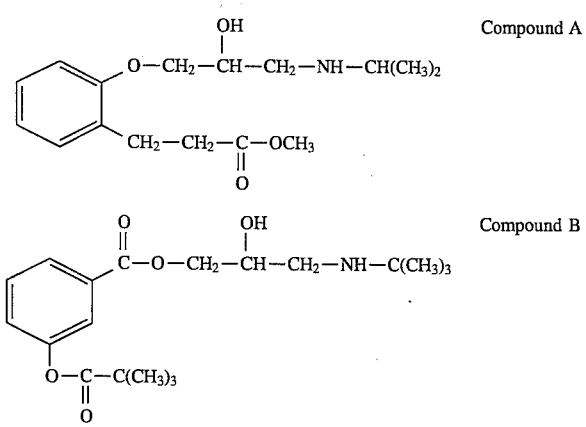

TABLE 1

| Compound (Dose) | Beta-Blockade Onset (minutes)[1] | Peak Blockade (% Inhibition)[2] | Time to Peak Blockade (minutes)[3] | Time to 50% Recovery from Blockade (minutes)[4] |
|---|---|---|---|---|
| A (0.16 mpk)[5] | 1–2 | 35 ± 6 | 10 | 38 |
| B | | | | |
| (0.16 mpk) | 3–4 | 39 ± 2 | 10 | 43 |
| (0.47 mpk) | 2–3 | 65 ± 4 | 10 | 81 |

[1]Defined as the time from sublingual dosing to the first detectable decrease in heart rate.
[2]Defined as the percent of reduction in isoproterenol-induced tachycardia.
[3]Defined as the times from sublingual dosing to the peak blockade of isoproterenol observed. (Isoproterenol dose every ten minuets.)
[4]Defined as the time from peak blockade to the decay of blockade by 50% of the peak.
[5]Dose mpk is mg/kg.

Pharmaceutical compositions for use in accordance with the present invention may be formulated in a conventional manner using one or more physiologically acceptable carriers or excipients.

Thus, the compounds of Formula I and their physiologically acceptable salts and solvates may be formulated for sublingual or buccal administration or in a form suitable for administration by inhalation or insufflation (through the mouth or nose). Sublingual and intranasal administration are particularly important.

For sublingual or buccal administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulfate). Liquid preparations for sublingual or buccal administration may be in the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparation may also contain buffer salts, flavoring, coloring and sweetening agents as appropriate.

Preparations for sublingual or buccal administration may be suitably formulated to give controlled release of the active compound.

The compounds of Formula I may be formulated for intranasal administration in the form of drops or spray. Intranasal compositions may take such forms as suspensions, solutions or emulsions in oily or aqueous vehicles and may contain formulatory agents such as thickening, suspending, stabilizing and/or dispersing agents and preservatives. Alternately, the active ingredient may be in powder form for constitution with a suitable vehicle, e.g., sterile pyrogen-free water, before use.

A proposed single dose of a compound of Formula I for use according to the invention for administration to man (of approximately 70 kg body weight) is about 0.1 to 100 mg, expressed as the weight of free base. A preferred single dose of active ingredient is about 10 to 40 mg. The single dose may be administered, for example, 1 to 6 times per day. The dose will depend on the route of administration of the compound used and on the age and weight of the patient as well as the severity of the condition to be treated. In particular circumstances it may be preferable to use a compound with a very short duration of action but relatively longer acting compounds may be preferred in other circumstances.

What is claimed is:

1. A method for the treatment or prophylaxis of disease states which are responsive to attenuation of sympathetic nervous system activity by beta blockers and wherein rapid alleviation or prevention of symptoms is critical, in a patient in need of such treatment, such method comprising the sublingual, buccal or intranasal administration to such patient of a therapeutically effective amount of a beta-blocking ester compound of the formula

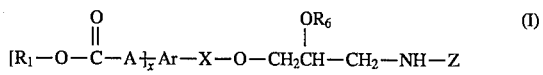

wherein

X is a direct bond or

Z is $(CH_2)_yB$ or

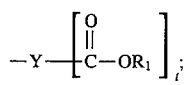

x is 0–3; y is 0–10; t is 0–3;

B, when y is 0, is lower alkyl, lower hydroxyalkyl, lower alkenyl, lower alkynyl or aralkyl;

B, when y is 1–10, is $-NR_2COR_3$, $-NR_2CONR_3R_4-$ $NR_2SO_2R_3$, $-NR_2SO_2NR_3R_4$ or $-NR_2COOR_5$; wherein $R_2$, $R_3$, $R_4$ and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_4$ are not hydrogen when B is $-NR_2SO_2R_3$ or $-NR_2COOR_5$;

Y is $C_1$–$C_6$ straight or branched carbon chain, or aralkyl; and $R_6$ is hydrogen or $-COJ$ wherein J is lower alkyl; wherein R1 is lower alkyl, lower cycloalkyl, lower alkenyl, lower alkynyl, lower alky carboxymethyl, aryl carboxymethyl, aryl, or aralkyl;

A is a direct bond, lower alkylene, or lower alkenylene; provided that when x is greater than 1, different occurrences of the

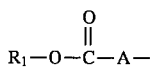

group may be the same or different; Ar is heterocyclic, unsubstituted aromatic or aromatic substituted with lower alkyl, lower alkenyl, lower alkynyl, lower alkoxy, halogen, acetamido, amino, lower alkylcarbonyloxy, nitro, lower alkylamino, hydroxy, lower hydroxyalkyl or cyano;

$R_8$, $R_9$ and $R_{10}$ are hydrogen or hydroxyl groups or the combination of either hydrogen or hydroxyl groups, or

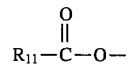

wherein $R_{11}$ is $C_1$–$C_6$ alkyl;

G represents straight or branched alkylene of from 1 to about 10 carbon atoms; and K represents hydrogen, $-NHCOR_{12}$, $-NHCONR_{12}R_{13}$, or $-NHCOOR_{13}$ wherein $R_{12}$ and $R_{13}$ may be the same or different and represent hydrogen, alkyl of from 1 to about 6 carbon atoms, alkoxyalkyl wherein the alkyl groups may be the same or different and contain from 1 to about 6 carbon atoms, cycloalkyl of from 3 to about 8 carbon atoms, alkenyl of from 2 to about 6 carbon atoms, alkynyl of from 2 to about 6 carbon atoms, phenyl which may be unsubstituted or substituted with alkyl of 1 to 6 carbon atoms, furanyl, thiophenyl, imidazole, oxazole or indole, aralkyl wherein the alkyl group contains from 1 to about 6 carbon atoms and the aryl group represents phenyl unsubstituted or substituted with alkyl of from 1 to about 6 carbon atoms, or $R_{13}$ and $R_{14}$ may together with N form a pyrrolidine, piperidine, piperazine, morpholine or thiomorpholine ring and $-NHCOOR_{13}$; and $R_{12}$ may be straight or branched lower alkyl, amino, cyclohexyl, morpholino, piperidino, tetrahydrofuranyl, dihydrofuranyl, tetrahydropyranyl, dioxolanyl, 2,2-dimethyl dioxolanyl, dioxanyl, pyrrolidinyl tetrahydroozazolyl, and dihydrooxazolyl, or a pharmaceutically acceptable salt thereof.

3. The method of claim 2 wherein the compound administered is of the formula

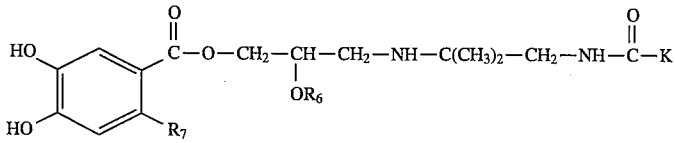

and pharmaceutically acceptable salts thereof; which beta-blocking ester compound is rapidly inactivated in vivo by ester hydrolysis so that the systemic half-life of effect of the compound is less than about 60 minutes.

2. The method of claim 1 wherein the compound administered is of the formula.

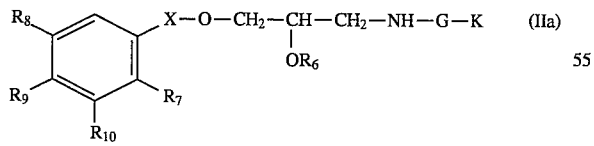

wherein $R_7$ is H, $C_1$–$C_6$ alkyl, $C_2$–$C_6$ alkenyl, $C_2$–$C_{10}$ alkynyl, halo, $C_1$–$C_6$ alkoxy, $C_1$–$C_6$ cycloalkyl, amino, acylamino, acetamido, nitro, $C_1$–$C_6$ alkylamino, hydroxy, $C_1$–$C_6$ hydroxyalkyl, cyano or arylalkoxy wherein the alkyl group includes 1–6 carbon atoms;

wherein $R_7$ is hydrogen, straight or branched lower alkyl, cycloalkyl, amino, lower alkoxy or acylamino, and K is straight or branched lower alkyl, amino, cyclohexyl, phenyl or phenyl substituted with lower alkyl, lower alkoxy or halo, benzyl, morpholino, piperiding, tetrahydrofuranyl, dihydrofuranyl, furanyl, tetrahydropyranyl, dioxolanyl, 2,2-dimethyl dioxolanyl, dioxanyl, pyrrolidinyl, tetrahydropyranyl, dioxolanyl, 2,2-dimethyl dioxolanyl, dioxanyl, pyrrolidinyl, tetrahydrooxazolyl, and dihydrooxazolyl $R_6$ is hydrogen or -COJ wherein J is straight or branched lower alkyl, and pharmaceutically acceptable salts thereof.

4. The method of claim 3 wherein $R_7$ is methyl, $R_6$ is hydrogen or t-butylcarbonyl and K is tetrahydrofuranyl.

5. The method of claim 2 wherein the compound administered is of the formula

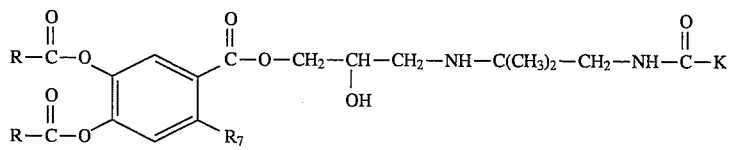

wherein

R is straight or branched lower alkyl;

R₇ is hydrogen, straight or branched lower alkyl, lower cycloalkyl, amino lower alkoxy or acylamino; and K is straight or branched lower alkyl, amino, cyclohexyl, morpholino, piperidino, tetrahydrofuranyl, dihydrofuranyl, tetrahydropyranyl, dioxolanyl, 2,2-dimethyl, dioxolanyl, dioxanyl, pyrrolidinyl, tetrahydrooxazolyl, and dihydrooxazolyl, and pharmaceutically acceptable salts thereof.

6. The method of claim 5 wherein R is t-butyl, R₇ is methyl and K is tetrahydrofuranyl.

7. The method of claim 2 wherein the compound administered is of the formula

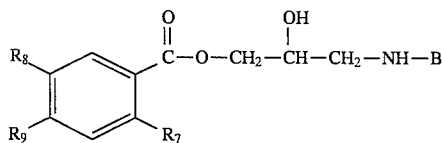

wherein R₇ is hydrogen, lower alkyl, cycloalkyl, amino, lower alkoxy or acylamino R₈ and R₉ are hydrogen, hydroxy, lower alkylcarbonyloxy, and may be the same or different B is lower alkyl, lower hydroxyalkyl, lower alkenyl, lower alkynyl or aralkyl and pharmaceutically acceptable salts thereof.

8. The method of claim 7 wherein B is isopropyl or t-butyl.

9. The method of claim 1 which comprises the sublingual administration of a beta-blocking ester compound.

10. The method of claim 1 which comprises the buccal administration of a beta-blocking ester compound.

11. The method of claim 1 which comprises the intranasal administration of a beta-blocking ester compound.

12. The method of claim 1 wherein said dosing is then terminated to thereby effect a rapid recovery of said patient from the beta-blocking effects of the compound.

13. A method for the treatment or prophylaxis of disease states which are responsive to attenuation of sympathetic nervous system activity by beta blockers and wherein rapid alleviation or prevention of symptoms is critical, in a patient in need of such treatment, such method comprising the sublingual, buccal or intranasal administration to such patient of a therapeutically effective amount of a beta-blocking ester compound of the formula

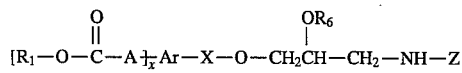 (I)

wherein

X is a direct bond or

Z is $(CH_2)_y B$ or

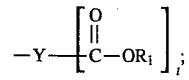

x is 0–3; y is 0–10; t is 0–3;

B, when y is 0, is lower alkyl, lower hydroxyalkyl, lower alkenyl, lower alkynyl or aralkyl;

B, when y is 1–10, is —NR₂COR₃, —NR₂CONR₃R₄, —NR₂SO₂R₃, —NR₂SO₂NR₃R₄ or —NR₂COOR₅; wherein R₂, R₃, R₄ and R₅ may be the same or different and may be hydrogen, alkyl, alkoxyalkyl, alkoxyaryl, cycloalkyl, alkenyl, alkynyl, aryl, heteroaryl, or aralkyl, except that R₃ and R₄ are not hydrogen when B is —NR₂SO₂R₃ or —NR₂COOR₅;

Y is C₁—C₆ straight or branched carbon chain, or aralkyl; and

R₆ is hydrogen or —COJ wherein J is lower alkyl; wherein R1 is lower alkyl, lower cycloalkyl, lower alkenyl, lower alkynyl, lower alkyl carboxymethyl, aryl carboxymethyl, aryl, or aralkyl;

A is a direct bond, lower alkylene, or lower alkenylene; provided that when x is greater than 1, different occurrences of the

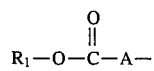

group may be the same or different; Ar is heterocyclic, unsubstituted aromatic or aromatic substituted with lower alkyl, lower alkenyl, lower alkynyl, lower alkoxy, halogen, acetamido, amino, lower alkylcarbonyloxy, nitro, lower alkylamina, hydroxy, lower hydroxyalkyl or cyano;

and pharmaceutically acceptable salts thereof, which beta-blocking ester compound is rapidly inactivated in vivo by ester hydrolysis so that the systemic half-life of effect of the compound is less than about 60 minutes; wherein additional sublingual, buccal or intranasal dosing of the beta-blocking ester compound may be given at 5 to 30 minute intervals to rapidly establish effective levels of beta blockade in said patient and then terminating said dosing to thereby effect a rapid recovery of said patient from the beta blocking effects or side effects of the compound.

14. The method of claim 13 which comprises the sublingual administration of a beta-blocking ester compound.

15. The method of claim 13 which comprises the buccal administration of a beta-blocking ester compound.

16. The method of claim 13 which comprises the intranasal administration of a beta-blocking ester compound.

17. A method for the treatment or prophylaxis of disease states which are responsive to attenuation of sympathetic nervous system activity by beta blockers, said disease states being selected from the group consisting of myocardial ischemia, angina, myocardial infarction, anxiety and migraine and wherein rapid alleviation or prevention of symptoms is critical, in a patient in need of such treatment, such method comprising the sublingual, buccal or intranasal administration to such patient of a therapeutically effective amount of a beta-blocking ester compound of the formula

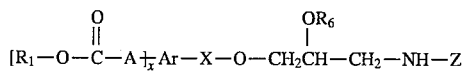

wherein

X is a direct bond or

Z is $(CH_2)_y B$ or

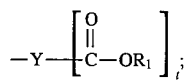

x is 0–3; y is 0–10; t is 0–3;

B, when y is 0, is lower alkyl, lower hydroxyalkyl, lower alkenyl, lower alkynyl or aralkyl; B, when y is 1–10, is $-NR_2COR_3$, $-NR_2CONR_3R_4$, $-NR_2SO_2R_3$, $-NR_2SO_2NR_3R_4$ or $-NR_2COOR_5$; wherein $R_2$, $R_3$, $R_4$ and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_4$ are not hydrogen when B is $-NR_2SO_2R_3$ or $-NR_2COOR_5$;

Y is $C_1$–$C_6$ straight or branched carbon chain, or aralkyl; and $R_6$ is hydrogen or —COJ wherein J is lower alkyl; wherein R1 is lower alkyl, lower cycloalkyl, lower alkenyl, lower alkynyl, lower alkyl carboxymethyl, aryl carboxymethyl, aryl, or aralkyl;

A is a direct bond, lower alkylene, or lower alkenylene; provided that when x is greater than 1, different occurrences of the

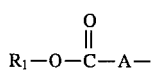

group may be the same or different; Ar is heterocyclic, unsubstituted aromatic or aromatic substituted with lower alkyl, lower alkenyl, lower alkynyl, lower alkoxy, halogen, acetamido, amino, lower alkylcarbonyloxy, nitro, lower alkylamino, hydroxy, lower hydroxyalkyl or cyano;

and pharmaceutically acceptable salts thereof; which beta-blocking ester compound is rapidly inactivated in vivo by ester hydrolysis so that the systemic half-life of effect of the compound is less than about 60 minutes.

18. The method of claim 17 which comprises the sublingual administration of a beta-blocking ester compound.

19. The method of claim 17 which comprises the buccal administration of a beta-blocking ester compound.

20. The method of claim 17 which comprises the intranasal administration of a beta-blocking ester compound.

21. A method for the treatment or prophylaxis of disease states which are responsive to attenuation of sympathetic nervous system activity by beta blockers, said disease states being selected from the group consisting of myocardial ischemia, angina, myocardial infarction, anxiety and migraine and wherein rapid alleviation or prevention of symptoms is critical, in a patient in need of such treatment, such method comprising the sublingual, buccal or intranasal administration to such patient of a therapeutically effective amount of a beta-blocking ester compound of the formula

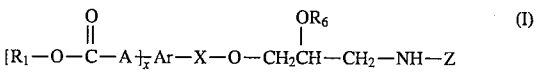

wherein

X is a direct bond or

z is $(CH_2)_y B$ or

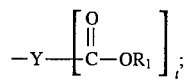

x is 0–3; y is 0–10; t is 0–3;

B, when y is 0, is lower alkyl, lower hydroxyalkyl, lower alkenyl, lower alkynyl or aralkyl;

B, when y is 1–10, is $-NR_2COR_3$, $-NR_2CONR_3R_4$, $-NR_2SO_2R_3$, $-NR_2SO_2NR_3R_4$ or $-NR_2COOR_5$; wherein $R_2$, $R_3$, $R_4$ and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_4$ are not hydrogen when B is $-NR_2SO_2R_3$ or $-NR_2COOR_5$;

Y is $C_1$–$C_6$ straight or branched carbon chain, or aralkyl; and

R6 is hydrogen or —COJ wherein J is lower alkyl; wherein R1 is lower alkyl, lower cycloalkyl, lower alkenyl, lower alkynyl, lower alky carboxymethyl, aryl carboxymethyl, aryl, or aralkyl;

A is a direct bond, lower alkylene, or lower alkenylene; provided that when x is greater than 1, different occurrences of the

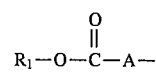

group may be the same or different; Ar is heterocyclic, unsubstituted aromatic or aromatic substituted with lower alkyl, lower alkenyl, lower alkynyl, lower alkoxy, halogen, acetamido, amino, lower alkycarbonyloxy, nitro, lower alkylamino, hydroxy, lower hydroxyalkyl or cyano; and pharmaceutically acceptable salts thereof; which beta-blocking ester compound is rapidly inactivated in vivo by ester hydrolysis so that the systemic half-life of effect of the compound is less than about 60 minutes; wherein additional dosing of the beta-blocking ester compound may be given at 5 to 30 minute intervals to rapidly establish effective levels of beta blockade in said patient and then terminating said dosing to thereby effect a rapid recovery of said patient from the beta blocking effects or side effects of the compound.

22. The method of claim 21 which comprises the sublingual administration of a beta-blocking compound.

23. A method for the treatment or prophylaxis of disease states which are responsive to attenuation of sympathetic nervous system activity by beta blockers, said disease states being selected from the group consisting of myocardial ischemia, angina, myocardial infarction, anxiety and migraine and wherein rapid alleviation or prevention of symptoms is critical, in a patient in need of such treatment, such method comprising the sublingual, buccal or intranasal administration to such patient of a therapeutically effective amount of beta-blocking ester compound of the formula

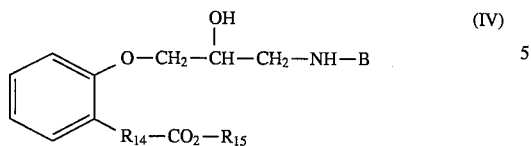

wherein $R_{14}$ is a direct bond or $C_1$–$C_6$ straight or branched alkyl, $C_1$–$C_6$ alkenyl and B are $C_1$–$C_6$ straight or branched alkyl, or pharmaceutically acceptable salts thereof; which beta-blocking ester compound is rapidly inactivated in vivo by ester hydrolysis so that the systemic half-life of effect of the compound is less than about 60 minutes.

24. A method of claim 23 wherein B is isopropyl or t-butyl and $R_{15}$ is methyl or ethyl.

25. A method of claim 23 wherein $R_{14}$ is a direct bond.

26. A method of claim 23 wherein $R_{14}$ is ethylenyl.

27. A method of claim 23 wherein $R_{14}$ is ethenyl.

28. A method of claim 23 wherein $R_{14}$ is propylenyl.

* * * * *